(12) United States Patent
Bruchhausen et al.

(10) Patent No.: US 9,383,303 B2
(45) Date of Patent: Jul. 5, 2016

(54) APPARATUS AND METHOD FOR CARRYING OUT IN A CONTROLLED ATMOSPHERE MATERIAL FATIGUE TESTS IN A HIGH CYCLE REGIME WITH A CONTROLLED STRAIN RATIO

(75) Inventors: Matthias Bruchhausen, Alkmaar (NL);
Peter Hahner, Alkmaar (NL);
Burkhard Fischer, Schagen (NL);
Daniel Cornu, Mantes la Jolie (FR);
Christophe Hurel, Limay (FR);
Jean-Pierre Lecornu, Courcelles sur Seine (FR)

(73) Assignees: SNECMA, Paris (FR); THE EUROPEAN UNION represented by the European Commission, Brussels (BE)

(*) Notice: Subject to any disclaimer, the term of this patent is extended or adjusted under 35 U.S.C. 154(b) by 372 days.

(21) Appl. No.: 14/234,274

(22) PCT Filed: Jul. 22, 2011

(86) PCT No.: PCT/IB2011/002430
§ 371 (c)(1),
(2), (4) Date: Mar. 21, 2014

(87) PCT Pub. No.: WO2013/014487
PCT Pub. Date: Jan. 31, 2013

(65) Prior Publication Data
US 2014/0245833 A1    Sep. 4, 2014

(51) Int. Cl.
*G01N 3/32* (2006.01)
*G01N 3/12* (2006.01)
*G01N 3/38* (2006.01)

(52) U.S. Cl.
CPC .. *G01N 3/32* (2013.01); *G01N 3/12* (2013.01);
*G01N 3/38* (2013.01); *G01N 2203/005* (2013.01); *G01N 2203/0008* (2013.01); *G01N 2203/0073* (2013.01); *G01N 2203/023* (2013.01)

(58) Field of Classification Search
CPC ............. G01N 3/12; G01N 3/38; G01N 3/32; G01N 2203/0008; G01N 2203/0073; G01N 2203/023; G01N 2203/005
USPC .......................................................... 73/571
See application file for complete search history.

(56) References Cited

U.S. PATENT DOCUMENTS

| 3,563,086 A | 2/1971 | Reed, Jr. |
| 3,633,403 A | 1/1972 | McDonald et al. |

(Continued)

FOREIGN PATENT DOCUMENTS

WO    2011/062322 A1    5/2011

OTHER PUBLICATIONS

International Search Report and Written Opinion of the International Searching Authority issued Feb. 24, 2012, in PCT/IB2011/002430, filed Jul. 22, 2011.

(Continued)

*Primary Examiner* — J M Saint Surin
(74) *Attorney, Agent, or Firm* — Oblon, McClelland, Maier & Neustadt, L.L.P.

(57) ABSTRACT

An apparatus for carrying out high cycle fatigue tests of a specimen under high pressure, including: a pressure vessel; a load train including a first horn and a second horn between which a specimen is to be arranged, wherein the load train is arranged within an internal chamber of the pressure vessel; and a converter configured to apply ultrasonic waves into the load train by exciting the first horn to apply a dynamic stress to the specimen. A base part of the second horn is movably seated in the pressure vessel such that two separated chambers are formed within the pressure vessel with the first chamber for the specimen, wherein both chambers can be fed with gas and charged with different gas pressures in order to apply a static stress to the specimen.

15 Claims, 5 Drawing Sheets

(56) References Cited

U.S. PATENT DOCUMENTS

| | | |
|---|---|---|
| 3,690,162 A | 9/1972 | Stecher |
| 4,107,982 A | 8/1978 | Mitsui et al. |
| 4,748,854 A | 6/1988 | Rao |
| 6,023,980 A | 2/2000 | Owen et al. |
| 6,575,620 B1 * | 6/2003 | Banaszak ............... G01N 3/068 374/4 |
| 6,601,456 B1 * | 8/2003 | Davidson ................ G01N 3/56 73/7 |
| 6,813,960 B1 * | 11/2004 | Owen ...................... G01N 3/32 73/794 |
| 2002/0017144 A1 | 2/2002 | Miles et al. |
| 2007/0187386 A1 * | 8/2007 | Kim ....................... H01L 21/324 219/385 |

OTHER PUBLICATIONS

Sumio Takahashi, et al., "Fatigue Test of Piezoelectric Ceramics under High Hydrostatic Pressure", Japanese Journal of Applied Physics, $10^{th}$ Symp. on Ultrasonic Electronics, vol. 29, No. 29, XP 000266229, 1990, pp. 47-49.

Won-Jong Lee, et al., "Electrohydraulic fatigue apparatus for testing in ultrahigh vacuum and controlled environments", Review of Scientific Instruments, vol. 57, No. 11, XP 002067422, Nov. 1986, pp. 2854-2858.

* cited by examiner

APPARATUS AND METHOD FOR CARRYING OUT IN A CONTROLLED ATMOSPHERE MATERIAL FATIGUE TESTS IN A HIGH CYCLE REGIME WITH A CONTROLLED STRAIN RATIO

TECHNICAL FIELD

The present invention relates to an apparatus and method for carrying out in a controlled atmosphere material fatigue tests of a specimen in a high cycle regime with a controlled strain ratio.

The invention more specifically relates to high cycle fatigue (HCF) testing of materials in a very high cycle regime (beyond $10^5$ cycles) by means of ultrasonic excitation with a variable strain ratio R between minimum strain and maximum strain and at variable pressure level environment.

The invention enables in particular to improve the characterization of different materials for space applications in presence of hazardous atmospheres such as hydrogen atmosphere under long duration mechanical dynamic loads.

The work leading to this invention has received funding from the European Union Seventh Framework Programme (FP7/2007-2013) under "grant agreement" n° 218849.

BACKGROUND OF THE INVENTION

Mechanical properties of materials are conventionally expressed by their yield strength (elastic limit) and ultimate tensile strength during unidirectional tensile loading.

Another parameter of importance is material fatigue, which is the progressive and localized structural damage that occurs when a material is subjected to cyclic loading. In this context it is of interest to study the fatigue of a sample at non-zero static load or to add a high-frequency cyclic load to low frequency fatigue.

FR 2 680 003 discloses a device for fatigue testing of materials that has been developed for the industry of gas turbines and the space industry and that makes it possible to simultaneously apply, to a specimen, a constant or slowly varying tensile force and longitudinal and/or transverse vibrational fatigue forces of adjustable amplitude. The device includes a hydraulic jack, which makes it possible to exert either a constant tension or set a cyclic tension, as well as two ultrasonic transducers operating at frequencies lying between 10 and 100 kHz. The specimen is arranged between a pair of horns (i.e. displacement amplifiers). The device further includes a static force transmission system consisting of a steel frame (or stirrup piece) and an optical device intended to measure the vibrational amplitude.

AT 354146 discloses another solution for testing a specimen in a high cycle fatigue regime and superposition of constant or variable loads and, hence, removing the constraint of symmetric push-pull mode.

For some applications, such as space applications, it is desirable to perform fatigue tests on specimen which are under controlled atmosphere, e.g. in the presence of hydrogen or other definite gas or mixture of gases which might be potentially dangerous and under high pressures, which may define a hazardous environment. The above, known devices do not readily allow to be used in combination with high pressures. Indeed, they rely on mechanical rods to transmit the constant part of the load to the specimen and would require feed throughs or bellows to be used under controlled atmospheres, which may be difficult at high pressures.

SUMMARY OF THE INVENTION

Therefore, it is an objective of the present invention to provide an apparatus and a method for carrying out high cycle fatigue tests on a specimen by means of ultrasonic excitation under high pressure and in potentially hazardous atmospheres such as hydrogen atmosphere with an improved safety and at controlled strain ratios R (where R=minimum strain/maximum strain). The concept enables a small gas working volume more favorable for safety design.

This objective is achieved with an apparatus and a method according to the invention as defined in the independent claims. Further embodiments of the invention are subject of the dependent claims.

A main idea underlying the present invention is to use a pressure vessel or autoclave for the specimen and to divide the pressure vessel into two chambers chargeable with different gas pressures so that a static stress can be induced in a load train arranged in the autoclave so that a specimen can be statically stressed within the autoclave and without the need of any feed throughs for rods or bellows. The difference of the gas pressures in the two chambers determines the application of a static stress on the specimen.

According to one aspect of the present invention, the invention relates to an apparatus for carrying out, in a controlled atmosphere, material fatigue tests of a specimen in a high cycle regime with a controlled strain ratio R, comprising:

a pressure vessel having an outer wall defining an internal chamber, a load train composed of a first horn and a second horn between which the specimen is to be arranged, wherein said load train has a longitudinal axis y'-y and is essentially arranged within said internal chamber of said pressure vessel, and a converter adapted to apply ultrasonic waves into the load train by exciting the first horn in order to apply a dynamic stress to the specimen in a direction parallel to said longitudinal axis y'-y, characterized in that said internal chamber is divided into a first chamber defining a free volume around at least a portion of said load train and a second chamber which is axially aligned with said first chamber along said longitudinal axis y'-y, said second horn comprising a base part which is partially and movably engaged into said second chamber to define in said second chamber a second free volume separated from the first free volume of said first chamber, a first gasket being interposed between said base part and a portion of the outer wall of said pressure vessel which is substantially parallel to said longitudinal axis y'-y to sealingly separate said first chamber from said second chamber, and first feeding means and second feeding means being provided for feeding said first and second free volumes of said first and second chambers with gases respectively having different gas pressures in order to apply a predetermined static stress to the specimen.

The concept of two chambers chargeable with different gas pressures allows replacing mechanical means such as rods or bellows for applying a static stress to the specimen. Thus, the risk of any leakage is significantly reduced, since no feed throughs for rods or the like are required, which enables testing even in an environment with hazardous atmosphere.

According to another aspect of the invention, the first horn comprises a base part having a cylindrical portion protruding out of the pressure vessel to be attached to the converter and a shoulder portion located opposite a portion of the outer wall of the pressure vessel which is substantially perpendicular to said longitudinal axis y'-y, a second gasket being provided at the interface between said shoulder portion and said portion of the outer wall to sealingly separate said base part of said first horn from said outer wall of said pressure vessel whilst enabling longitudinal oscillations of said first horn.

The first horn, the second horn, and the specimen are advantageously dimensioned in resonance with the frequency of the ultrasonic waves coupled by the converter into the load train and the first gasket and the second gasket as well as the center of the specimen are preferably located at nodes of displacement (i.e. at positions where the displacement amplitude is zero) of said load train where the stress is at a maximum.

This is helpful to optimize the application of stress to the specimen, and particularly to control the application of maximum stress whilst maintaining a constant pressure difference between both chambers which will lead to a constant stress applied to the specimen, or imposing a slowly varying cyclic pressure difference between both chambers which will lead to a slowly varying cyclic stress applied to the specimen.

It may be noted that term "horn" herein designates, as it is known to those skilled in the art, an element of generally tapering shape that acts as a resonant element and permits magnifying or amplifying the vibratory motion applied by the converter/transducer. In the most conventional designs, horns have a linear, exponential or stepped taper. Continuously tapering horn shapes (at least for the tip portion) are preferred as they allow an optimized application of stress on the specimen with a concentration of stress in the specimen, particularly with a maximum of stress in the middle part of the specimen (the specimen having preferably a hourglass shape with its narrowest section in the middle of the specimen). Thus the first and second horns are advantageously designed as members having a generally tapering shape from their base part to their tip which is connected to the specimen.

The base part of the second horn may comprise a peripheral groove fitted with a gasket for mainly sealingly separating the two chambers from each other. The gasket particularly serves to reduce leakage from one chamber into the other chamber.

According to an aspect of the invention, the first and second feeding means each comprise at least a source of gas having a predetermined composition, a control device to define a predetermined gas pressure, a gas conduit and at least one channel provided in the outer wall of the pressure vessel to be in communication with the first free volume or the second free volume respectively.

According to a specific embodiment, the first feeding means comprises a first source of gas having a predetermined composition, a control device to define a predetermined gas pressure for the gas taken from the first source of gas, a first gas conduit connected to said first source of gas and to an inlet channel outputting into said first free volume, and an outlet channel in communication with said first free volume and outputting into a second gas conduit connected to said first source of gas, said control device further defining a predetermined gas flow through the first free volume that is larger than a residual leakage flow between the first and second free volumes of the first and second chambers.

The pressure vessel may thus comprise at least one first channel to the upper chamber and at least one second channel to the lower chamber, wherein the channels are formed for supplying gas to the chambers and allow attachment of gas conduits. The channels hence enable the coupling of the apparatus with a gas flow control system, which enables the control of the static stress applied to the specimen by controlling the gas flows in the apparatus, particularly the pressure difference between both gas chambers within the pressure vessel.

The apparatus may further comprise a gas inlet and exhaust control device, which is adapted to maintain a nearly constant preset pressure difference between the first and second chambers. With a gas inlet and a gas exhaust associated with at least one chamber, a gas flow through said chamber may be established so that the chamber can be continuously charged with fresh gas.

The control device may be configured to control a gas composition in the first chamber, particularly by maintaining a gas flow through the first chamber that is larger than a leakage flow between the first and the second chambers.

The gas to be filled in the first chamber or the second chamber may be a pure gas such as for example hydrogen or argon, or a mixture of different gases such as for example a mixture of hydrogen and at least another gas such as argon.

This allows performing tests of a specimen in a required hazardous environment in the apparatus.

The apparatus may be designed for pressures in the first and second free volumes of the first and second chambers up to 1000 bar, as for example from 200 bar to 500 bar. This allows testing a specimen under high-pressure conditions and in hazardous atmosphere.

Preferably, the longitudinal axis y'-y of the load train is substantially vertical, the first horn defining an upper horn and the second horn defining a lower horn.

According to another aspect of the present invention, it is proposed a method for carrying out, in a controlled atmosphere, material fatigue tests of a specimen in a high cycle regime with a controlled strain ratio R with an apparatus of the invention as described above that is characterized in that it comprises the following steps:

locating a specimen within the first chamber of the apparatus by fixing the one end of the specimen to the tip of the first horn and fixing the opposite end of the specimen to the tip of the second horn, feeding gas in the first and second chambers of the pressure vessel such that due to a pressure difference in both first and second chambers a desired static stress is applied to the specimen, controlling the converter such that a dynamic stress is applied to the specimen by exciting ultrasonic waves coupled from the converter into the load train, and maintaining a nearly constant preset pressure difference between the first and second chambers by controlling the gas flow to the first and second chambers via said first and second feeding means.

If a pure gas is used to feed the first and second free volumes of the first and second chambers, the step of maintaining a nearly constant preset pressure difference between the first and second chambers may comprise: controlling an exhaust from the one of the first and second chambers having the lower pressure and increasing a gas flow into the other of the first and second chambers having a higher pressure such that a leakage flow between said first and second chambers is compensated.

Alternatively, if a gas mixture is used to feed the first and second free volumes of the first and second chambers, the step of maintaining a nearly constant preset pressure difference between the first and second chambers may comprise:

maintaining a predetermined gas flow through the one of the first and second chambers having the higher pressure, said predetermined gas flow being larger than a leakage flow between the first and the second chambers in order to control a gas composition in said one of the first and second chambers having the higher pressure.

The method thus comprises the act of maintaining a nearly constant preset pressure difference between the first and second chambers by controlling the gas flows to the chambers.

The above and other objects, features and advantages of the present invention will become apparent from the following description and the appended claims, taken in conjunction with the accompanying drawings in which like parts or elements are denoted by like reference symbols.

The invention will be described in more detail hereinafter with reference to exemplary embodiments. However, the invention is not limited to these exemplary embodiments.

DETAILED DESCRIPTION OF EMBODIMENTS OF THE INVENTION

Figure 1:
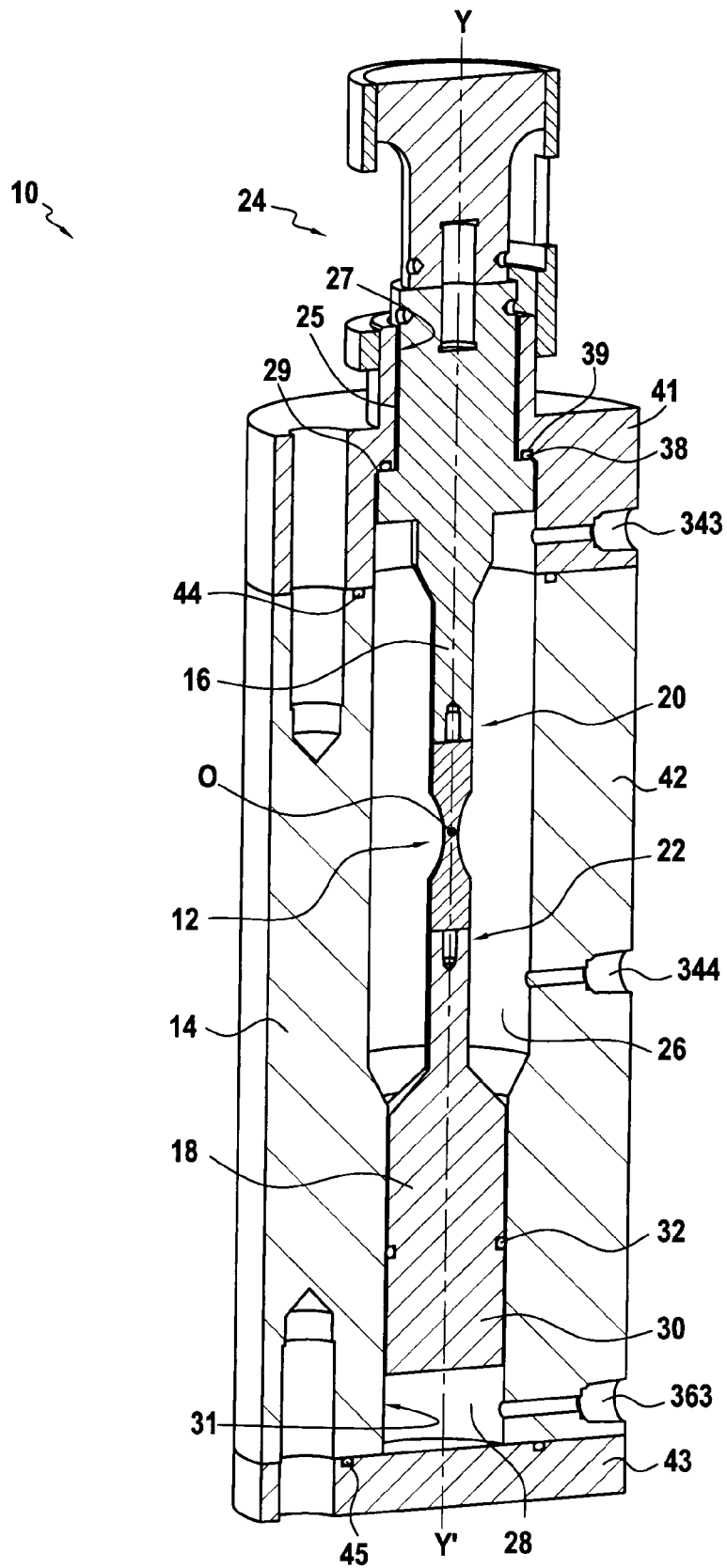
FIG. 1 shows a perspective view of an embodiment of the present apparatus for carrying out high cycle fatigue tests, the apparatus being shown in a half view cut along a longitudinal plane to better show the internal components.

In the following, functionally similar or identical elements may have the same reference numerals.

An apparatus according to the present invention allows fatigue testing of materials in a high cycle and very high cycle fatigue regime beyond $10^5$ cycles, e.g. with $10^9$ cycles by means of ultrasonic excitation. The apparatus permits carrying out these tests under high pressure in hazardous gases such as hydrogen and at controlled strain ratios R, wherein R=minimum strain/maximum strain.

An ultrasonic excitation of a specimen as disclosed in AT354146 results in a symmetric push-pull mode where compressive and tensile stresses have the same amplitudes. The strain ratio is −1 in this mode. However, in typical applications, cycling stress, for example from rotative parts of turbo machines, is superposed to a constant stress, for example from centrifugal stress, which makes testing at positive strain ratios more relevant.

For removing the constraint of working at a symmetric push-pull mode with R=−1 an additional (generally tensile) static or quasi-static stress should be applied to a specimen. This additional stress can be created according to the invention by means of a high pressure vessel, in which the specimen is located. The vessel is split into two chambers with different gas pressures, which can lead to a proportional force on the specimen.

FIG. 1 shows an embodiment of the apparatus 10 for testing a specimen 12 comprising a pressure vessel taking the form of an autoclave 14. Within the autoclave 14, in a first chamber 26 thereof, a load train comprising an upper, first horn 16 and a lower, second horn 18 is arranged. The specimen 12 is placed in this first chamber 26 between the horn tips 20, 22. A converter 24 (not completely shown) comprising an ultrasonic transducer for generating an ultrasonic excitation of the upper horn 16 is coupled to the latter. In this variant, the converter 24 is located outside the autoclave 14. Therefore, a cylindrical section 25 of the base of the first horn 16 is received in a through bore 27 in the top wall of the autoclave 14. The outer end of this cylindrical portion 25 is firmly attached to converter 24. Inside the first chamber 26, the cylindrical section 25 continues axially into a shoulder section or flanged portion 29. A gasket 38 is located in-between this shoulder section 29 and the sealing surface surrounding the through bore 27.

Vibrations of the cylindrical section 25 are authorized without creating a leakage due to the provision of a polymer seal 38 in the gap between the shoulder section 29 and a portion 39 of the outer wall of the autoclave 14 that is substantially perpendicular to the longitudinal axis y'-y of the load train.

The ultrasonic excitation is transmitted by the upper horn 16 to the specimen 12, which is located between the tip 20 (lower part in the FIGS. 1 and 2) of the upper horn 16 and the tip 22 (upper part in the FIGS. 1 and 2) of the lower horn 18. The specimen 12 is fixed with one end to tip 20 and with its other end to the tip 22, for example by means of screws or any other appropriate means. A base part 30 of the lower horn 18 is movably seated (and hence axially guided) in a lower part of the autoclave 14, more specifically in a blind bore 31. The length of this blind bore 31 is such that it may define a lower chamber 28 with a cavity remaining below the bottom horn 18. This cavity forms a free volume of the second chamber 28 and is defined by the bottom surface of the base part 30 of the second horn 18, the bore 31 and the bottom wall 43 of the autoclave 14.

A gasket 32 is installed in a peripheral groove in the base part 30 of the second horn 18 and thus obstructs the exchange of gas between the free volumes of the first and second chambers 26 and 28. While the flow of gas between the first and second chambers 26 and 28 is hindered by the gasket 32, the base part 30 of the lower horn 18 can still move within the blind bore 31 of the autoclave 14 when the load train is subjected to oscillations. The base part 30 may also accommodate different longitudinal positions according to the specimen tested to take into account the fact that the length of the specimen may vary depending on the tested material.

Both chambers 26 and 28 (i.e. the free volumes thereof) can be fed with gas in order to control the tensile or compressive stress applied to the specimen 12 in addition to the dynamic stress applied from the converter 24 via the upper horn 16 to the specimen 12. The applied stress essentially depends on the pressure difference of both chambers 26 and 28. A constant pressure difference between both chambers 26 and 28 leads to a constant stress applied to the specimen 12.

By adjusting the pressure difference between the pressure chambers, the position of the lower horn 18 may be slightly modified, because the stress on the load train will slightly change its length. However, in practice this change in length is very small (well below 1 mm) and does not significantly modify the actual position of the lower horn 18.

Figure 2:
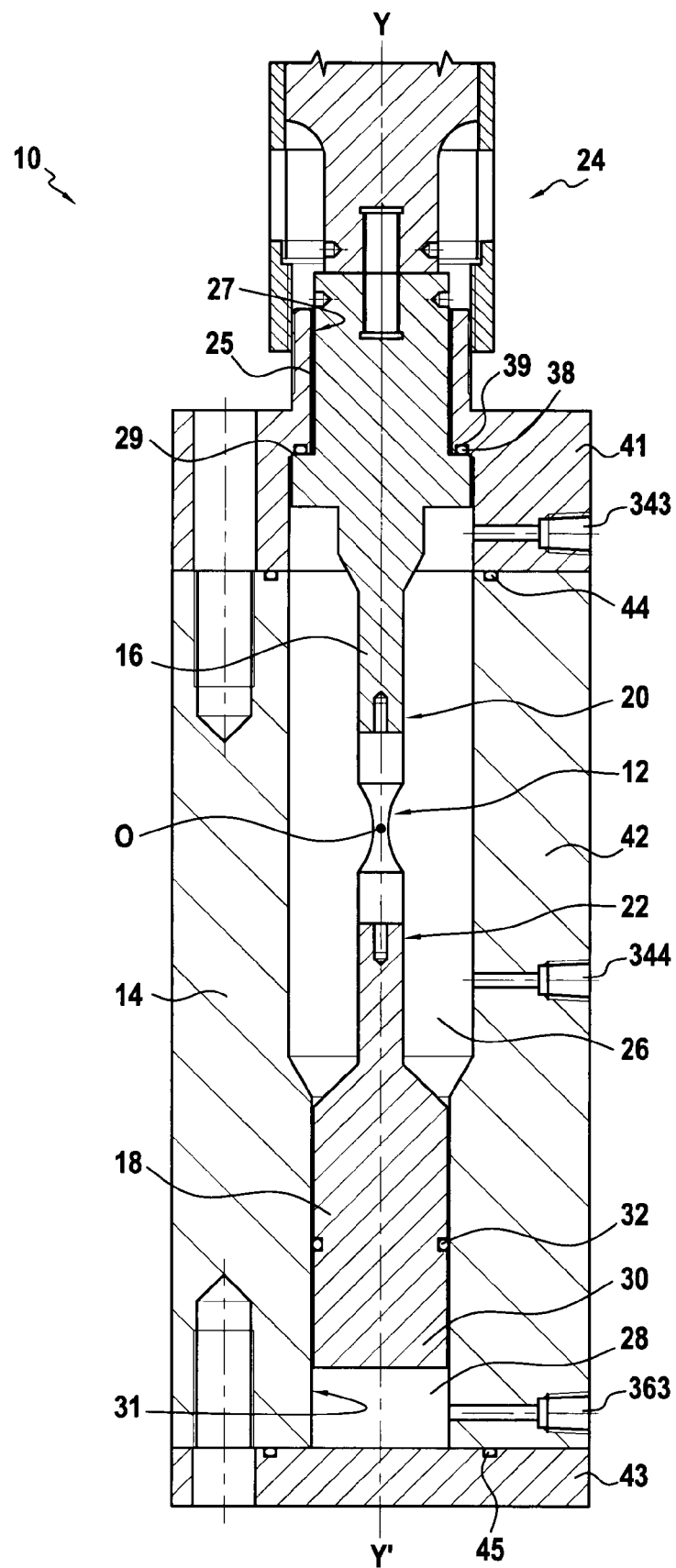
FIG. 2 shows a longitudinal cross-sectional view of the embodiment of FIG. 1.

FIG. 2 shows the apparatus 10 of FIG. 1 in a longitudinal cross-sectional view. The ultrasonic excitation of the upper horn 16 is carried out from the top by means for example of a commercially available converter 24 based on a piezoelectric crystal. In FIG. 2, only a part of the converter 24 is shown. The view of FIG. 2 shows a first channel 343 through the wall of the autoclave 14 to the upper, first chamber 26 and a second channel 363 through the wall of the autoclave 14 to the lower, second chamber 28. Both channels 343 and 363 allow attaching gas conduits (not shown in FIG. 2 but shown in FIG. 7 as conduits 342 and 362 respectively) to the autoclave 14 in order to control the pressure inside the chambers 26 and 28 and particularly maintain a desired pressure difference between both chambers 26 and 28 with a gas inlet and exhaust control device (not shown in FIG. 2 but shown as control devices 341, 361 in FIG. 7). The control devices 341, 361, which may be combined in a single unit, can be adapted to maintain a nearly constant pressure difference between both chambers 26 and 28.

The gas charged in the chambers 26 and 28 may be any gas suitable for defining a realistic environment for the specimen to be tested. It may be for example $H_2$ (Hydrogen), Ar (Argon), a mixture of these gases or other gases chosen according to the needs.

The perspective cross-sectional view of FIG. 1 and the cross-sectional view of FIG. 2 also show the shapes of the upper horn 16 and lower horn 18. The upper horn 16 has a diameter, which generally (except for the shoulder 29) tapers from the horn's base (upper) part 25 to the horn's tip 20 (lower part). The lower horn 18 is similarly shaped with its diameter generally tapering from its base 30 (lower part) to its tip 22 (upper part). Due to the progressive reduction of the diameter of the upper horn 16 to the center of the specimen 12 (preferably of hourglass shape), a maximum of (dynamic) stress can be incurred in the center of the specimen 12, so that a failure of specimen 12 will most likely occur in its center region O.

The lower horn 18 is not fixed inside the autoclave 14; it is only axially guided in the bore 31, and it is only connected with its tip 22 to the lower part of the specimen 12. When the pressure in the upper chamber 26 is larger than the pressure in the lower chamber 28, a static tensile stress is applied to the specimen 12 in addition to the dynamic stress incurred by the ultrasonic excitation. The ratio of the cross sections in the center of the specimen and at the gasket 32 separating the two chambers 26, 28 defines the amplification factor for the static load. The amplification factor multiplied with the pressure difference between the chambers 26 and 28 determines the static stress at the specimen's center.

The strain ratio R is the ratio of the lowest to the highest strain. If D is the amplitude of a sinusoidal strain (e.g. introduced by the ultrasonic excitation) and S the static strain (e.g. resulting from the pressure difference in the gas chambers 26 and 28), R can be written as $$R=(S-D)/(S+D) \text{ where } D \geq 0 \text{ and } S \text{ any value.}$$

Typical operational parameters of an embodiment of an apparatus according to the invention, which may be designed for a total pressure up to several hundreds bar, are listed in the following table for the sake of exemplification, but other values are also within the scope of the present invention:

| Pressure upper chamber | Up to 400 bar |
| --- | --- |
| Pressure lower chamber | Up to 400 bar |
| Excitation frequency | ≈20 kHz |
| Dynamic stress | <1000 MPa |
| Static stress | <1000 MPa |
| Strain ratio R | $-\infty < R < +1$ (e.g. <0.8) |
| Working gas | e.g. $H_2$ or Ar, as pure gas or mixture of gases |

The next table shows typical dynamic stress amplitudes, pressure differences and resulting strain ratios R:

| Dynamic stress [MPa] | Pressure difference [bar] | Static stress [MPa] | R |
| --- | --- | --- | --- |
| 410 | −50 | −400 | −81.00 |
| 500 | 0 | 0 | −1.00 |
| 400 | 50 | 400 | 0.00 |
| 100 | 100 | 800 | 0.78 |

In order to maintain the constant stress for achieving $R \neq -1$, a pressure difference between both chambers 26 and 28 is required. Consequently, there is a different pressure required in the upper chamber 26 than the pressure in the lower chamber 28. The embodiment of the apparatus can be operated with several gases as for example $H_2$ or Ar as working gases, but other types of gases may be used according to the needs.

In the present description, it has been considered that the pressure in the upper chamber 26 is higher than the pressure in the lower chamber 28. In such a case the specimen 12 is subjected to a static tensile stress in addition to the cyclic stress due to the ultrasonic excitation. However the pressure in the upper chamber 26 may be lower than the pressure in the lower chamber 28. In such a case the specimen 12 is subjected to a constant compressive stress in addition to the cyclic stress due to the ultrasonic excitation. Thus depending on which chamber 26 or 28 the higher pressure has, the force can either lead to tensile or compressive stress in the specimen 12, such tensile or compressive stress being superposed to the symmetrically alternating stress field created by the standing ultrasonic wave.

In the following, a practical embodiment of the apparatus according to the invention with an ultrasonic excitation frequency of 20 kHz is described, but this value is only given by way of example. The upper and lower horns 16, 18 as well as the specimen 12 are preferably specifically designed in accordance with the resonance condition at the excitation frequency. In particular, the positioning of the nodes of displacement (maxima of stress) within the horns 16, 18 and the specimen 12 are to be given careful attention for optimal operation. Two nodes of displacement should preferably be localized at the points where the upper gasket 38 (FIG. 2) terminates the autoclave 14 at the top and where the lower gasket 32 (FIG. 2) separates both pressure chambers 26 and 28 from each other. A third node should preferably be situated at the center O of the specimen 12. Since the length of the specimen 12 depends on the tested material, the position of the lower gasket 32 is fixed on the base part 30 of the lower horn 18 but may vary relative to the interior (blind bore 31) of the autoclave 14.

Since the base part 30 of the lower horn 18 defining the boundary separating the two gas chambers 26, 28 at the level of the gasket 32 is only rigidly connected by the tip 22 of the lower horn 18 to the specimen 12, but not to the outer wall of the pressure vessel 14 defining the blind bore 31 and the lower pressure chamber 28, the difference of the gas pressures in the two pressure chambers 26 and 28 leads to a proportional force on the specimen 12.

The pressure vessel or autoclave 14 may be constructed in different manners and the vertical position of the autoclave 14 of the illustrated example is only a preferred embodiment.

In the exemplified embodiment of FIG. 2, the autoclave comprises an upper portion 41 or cover part which is removable to allow for the insertion of the load train including the shoulder portion 29 of the base part of the upper horn 16. The upper portion 41 defines a substantially horizontal outer wall 39 which is located opposite the shoulder portion 29 of the upper horn 16 to define an interface where the gasket 38 is located. The upper portion 41 further defines the through bore 27 enabling the protrusion of the cylindrical portion 25 outside the autoclave 14 to be coupled with the converter 24. A gasket 44 is located between the upper portion 41 and a middle portion 42 defining the body of the autoclave 14. The upper portion 41 may be connected to the middle portion 42 through bolts, screws or any other known connecting means. The middle portion 42 is connected to a bottom portion 43 which constitutes a base plate and closes the lower chamber 28. A gasket 45 is inserted between the bottom portion 43 and the lower end portion of the middle portion 42. The bottom portion 43 may be connected to the middle portion through any known connection means such as bolts or alike.

Figure 3:
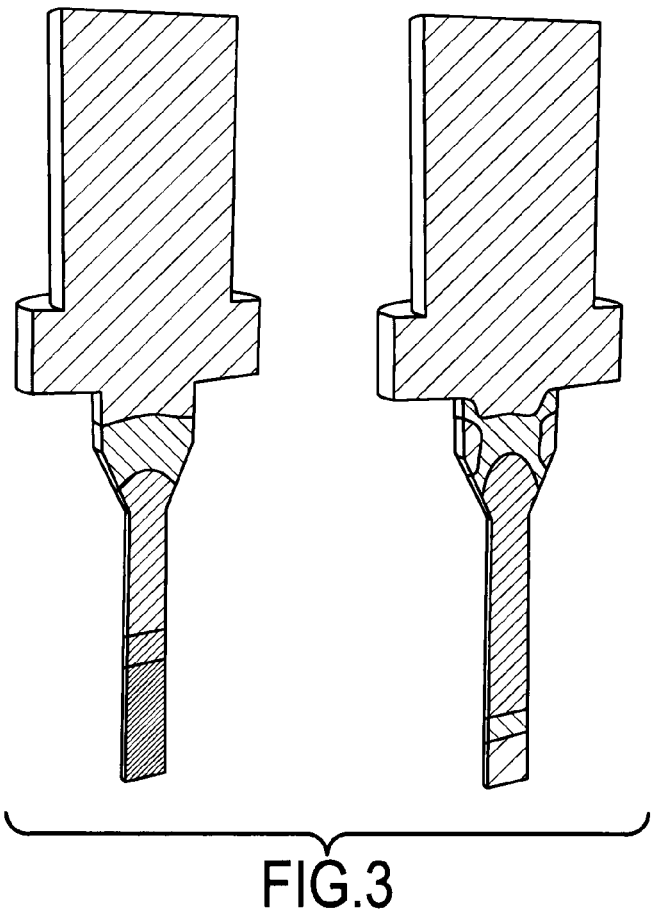
FIG. 3 shows results of FEM calculations of the distributions of axial displacement amplitude and axial stress amplitude in the upper horn of the embodiment of FIG. 1 under resonance conditions.
Figure 4:
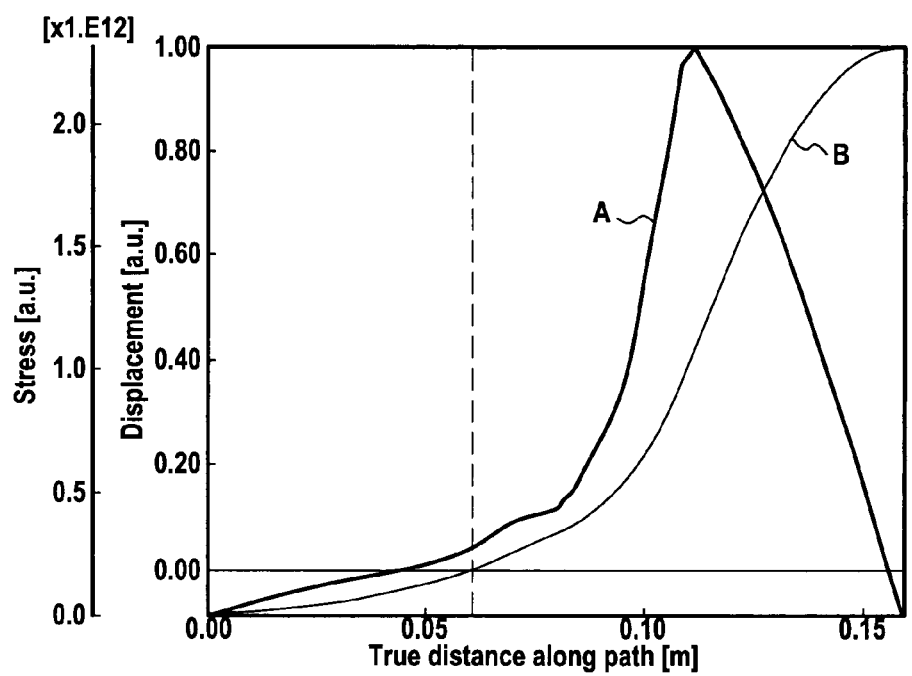
FIG. 4 shows a graph of the axial stress amplitude and displacement amplitude along the axis of the upper horn when excited in resonance in the embodiment of FIG. 1.

FIG. 3 shows FEM (Finite Element Method) calculations of the distributions of the axial displacement (left figure) and axial stress (right figure) in the upper horn 16 of this practical embodiment of the present apparatus under resonance conditions in the relevant mode. In FIG. 4, the curves A of axial stress amplitude and B of displacement amplitude are plotted along the axis of symmetry of the upper horn 16 when excited in resonance.

The node of displacement (displacement=0) represented as a dashed vertical line in FIG. 4 is located very close to the surface, where the flanged portion of the upper horn 16 will be in contact with the wall portion 39 of the gas vessel (interior of the autoclave) at the level of the gasket 38 (see FIG. 1 and FIG. 2). This serves to maintain the resonance condition when mounting the horn 16 in the upper flange 39 of the upper pressure chamber 26 of the autoclave 14. Due to its form, the horn 16 amplifies the excitation amplitude by approximately a factor of 10, which helps achieving high stress levels in the specimen 12.

In order to obtain high stress values for a given excitation amplitude, the geometry of the setup is optimized so that a maximum of the stress is localized in the centre O of the specimen 12 where its diameter is the smallest. This allows making the best use of an hourglass shaped geometry of the specimen 12, which leads to an increase of the stress in the centre O of the specimen 12 and defines the place where failure through fatigue will occur. The exact length of the specimen 12 depends on the tested material.

Figure 5:
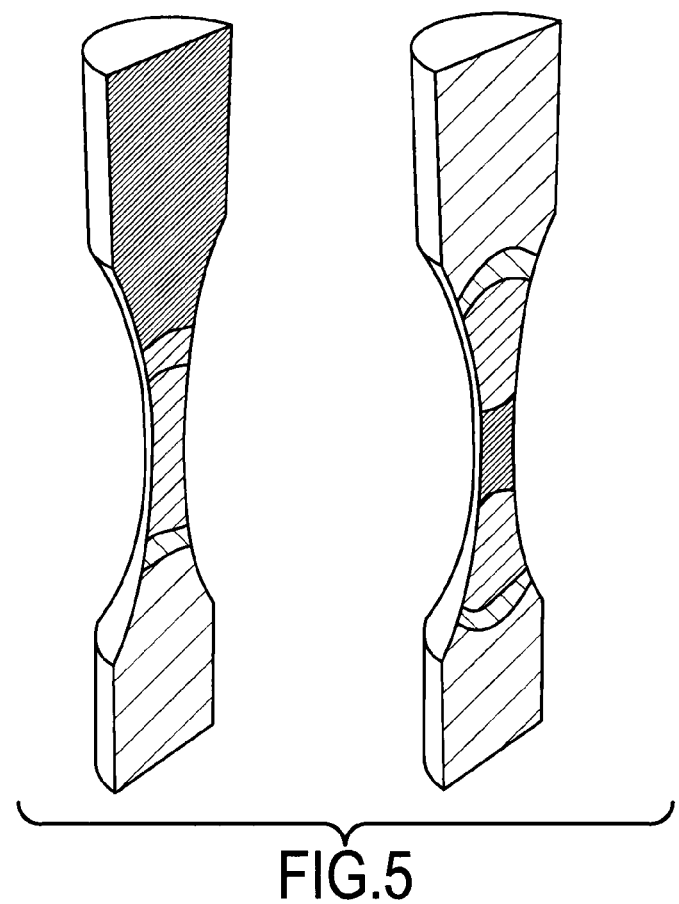
FIG. 5 shows results of FEM calculations of the distributions of normalized axial displacement amplitude and axial stress amplitude in the specimen tested in the embodiment of FIG. 1 under resonance conditions.

FIG. 5 shows the distribution of the normalized axial displacement amplitude (left view) and the axial stress amplitude (right view) on the specimen 12 under resonance conditions (in arbitrary units).

Figure 6:
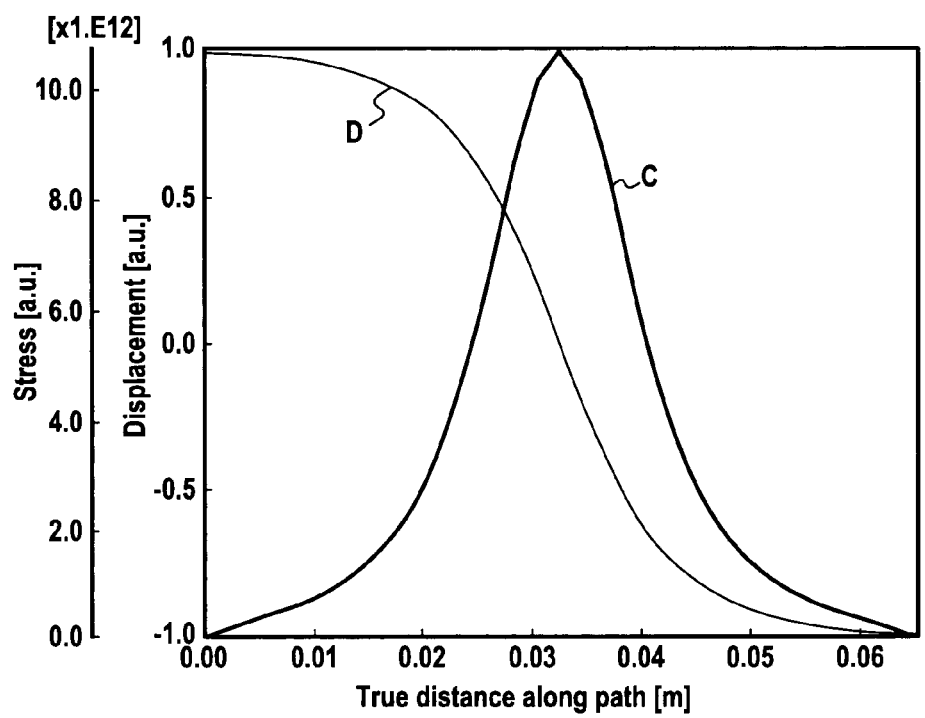
FIG. 6 shows a graph of the axial stress amplitude and displacement amplitude along the axis of the specimen when excited in resonance in the embodiment of FIG. 1.

The variation of the stress amplitude (curve C) and of the displacement amplitude (curve D) along the longitudinal axis y'-y of the specimen 12 when excited in resonance is displayed in FIG. 6. It can be clearly seen that the hourglass shape of the specimen 12 leads to an increase of the stress amplitude in the centre of the specimen 12.

Figure 7:
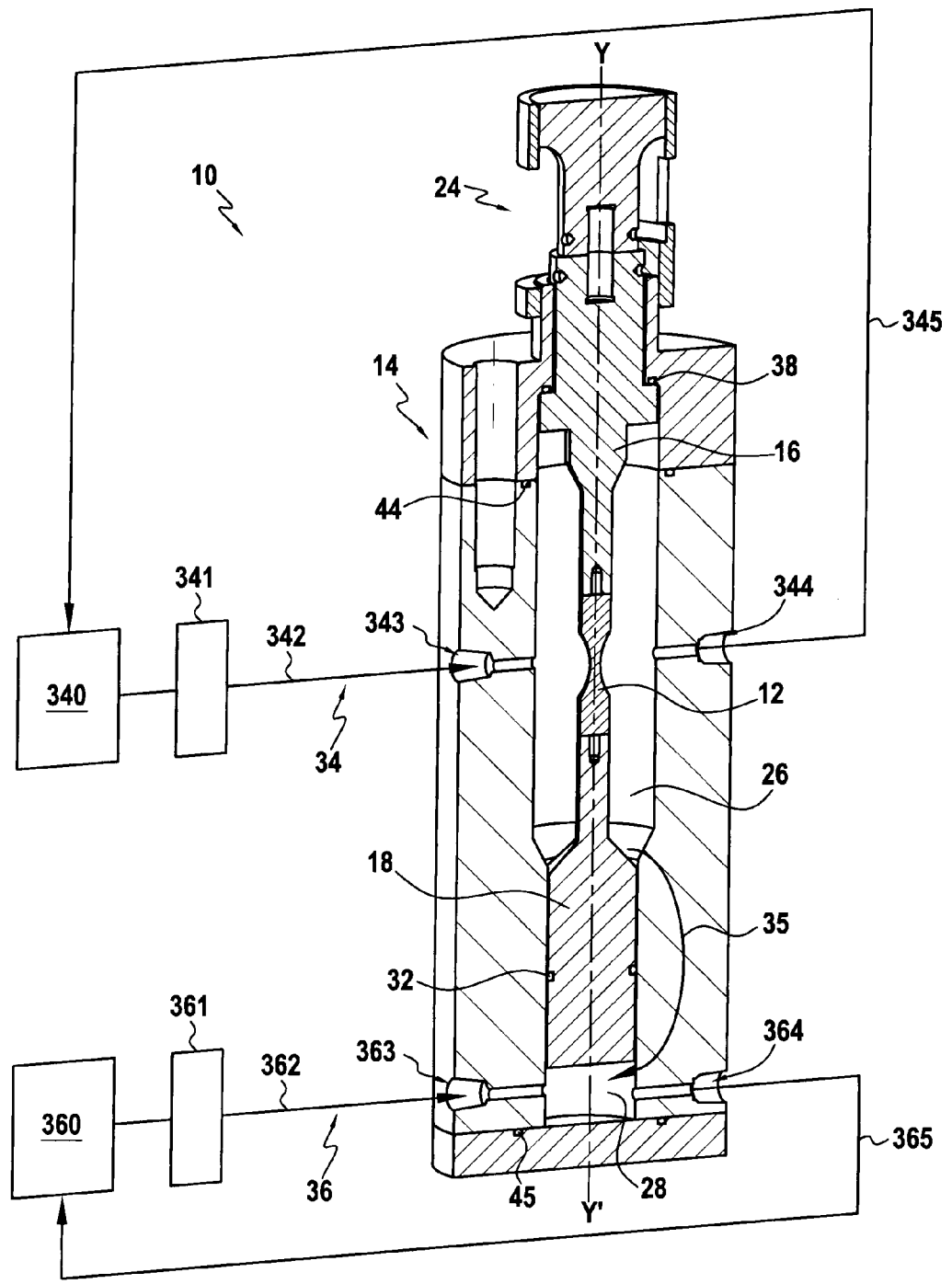
FIG. 7 shows an overview of gas flows in the embodiment of FIG. 1, as well as a block diagram of gas feeding units associated with the apparatus.

FIG. 7 shows an overview of the gas flows in the apparatus according to the invention. The main gas flows are used to control the respective pressures in the upper and lower chambers 26, 28. Difficulties may arise from a leakage flow 35 between the two chambers 26 and 28. In particular, this flow 35 might increase over time during a single measurement or test due to wear of the gasket 32 of the lower horn 18, especially if the gasket 32 is not positioned exactly at the node of displacement on the lower horn 18.

When operating in a pure gas atmosphere (e.g. Hydrogen alone or Argon alone or any other pure gas such as Helium), this leakage flow 35 can be compensated by a controlled exhaust from the lower chamber 28 and a corresponding increase of the gas flow into the upper chamber 26. In case of a gas mixture (e.g. a mixture of Hydrogen and Argon or any other gas or any other mixture of gases) as a working gas, the leakage flow 35 will be different for the different gas components of the mixture, which will have an impact on the gas composition in the upper chamber 26. The desired gas mixture in the upper chamber 26 can be assured by maintaining a gas flow through the upper chamber 26 that is larger than the leakage flow 35 between the chambers 26 and 28 so that there is always fresh gas in the upper chamber 26.

In FIG. 7 two separate gas sources 340, 360 for the first and second pressure chambers 26, 28 are schematically illustrated. The gas sources 340, 360 are supposed to deliver the required gas flows under the required pressures for the respective pressure chambers 26 and 28 as defined by control units 341 and 361 which may comprise in particular manometers and/or flowmeters. However, the system may comprise a common primary gas source and two separate control units for not only monitoring but also adjusting the flow and pressure of the gas serving to feed the respective first and second chambers 26, 28 through the lines 342 and 362.

An inlet line 342 and an exhaust line 345 are required for the first chamber 26 and an inlet line 362 and an exhaust line 365 are required for the second chamber 28 if the gas flows must be controlled. However inlet lines 342 and 362 could be used alone to feed the first and second chambers 26, 28 with gas under two different pressures, without exhaust line 345 and/or exhaust line 365 if it is not decided to maintain a gas flow in the first chamber 26 and/or the second chamber 28.

In summary the present invention removes the need of a direct mechanical contact from a high cycle fatigue testing machine to a specimen for generating a static stress. The invention particularly avoids any movable parts in a high-pressure environment and is therefore safer than testing machines using feedthroughs for rods or bellows in order to apply a static stress to a specimen.

While preferred embodiments of the present invention have been described using specific terms, such description is for illustrative purpose only, and it is to be understood that changes and variations may be made without departing from the scope of the following claims.

The invention claimed is:

1. An apparatus for carrying out, in a controlled atmosphere, material fatigue tests of a specimen in a high cycle regime with a controlled strain ratio, comprising:
   a pressure vessel having an outer wall defining an internal chamber,
   a load train composed of a first horn and a second horn between which the specimen is to be arranged, wherein said load train has a longitudinal axis and is essentially arranged within said internal chamber of said pressure vessel, and
   a converter adapted to apply ultrasonic waves into the load train by exciting the first horn in order to apply a dynamic stress to the specimen in a direction parallel to said longitudinal axis,
   wherein internal chamber is divided into a first chamber defining a free volume around at least a portion of said load train including said specimen and a second chamber which is axially aligned with said first chamber along said longitudinal axis, said second horn comprising a base part which is partially and movably engaged into said second chamber to define in said second chamber a second free volume separated from the first free volume of said first chamber, a first gasket being interposed between said base part and a portion of the outer wall of said pressure vessel which is substantially parallel to said longitudinal axis to sealingly separate said first chamber from said second chamber, and first feeding means and second feeding means being provided for feeding said first and second free volumes of said first and second chambers with gases respectively having different gas pressures in order to apply a predetermined static stress to the specimen.

2. The apparatus according to claim 1, wherein said first horn comprises a base part having a cylindrical portion protruding out of the pressure vessel to be attached to the converter and a shoulder portion located opposite a portion of the outer wall of the pressure vessel which is substantially perpendicular to said longitudinal axis, a second gasket being provided at the interface between said shoulder portion and said portion of the outer wall to sealingly separate said base part of said first horn from said outer wall of said pressure vessel whilst enabling longitudinal oscillations of said first horn.

3. The apparatus according to claim 2, wherein the first horn, the second horn, and the specimen having a center are dimensioned in resonance with the frequency of the ultrasonic waves coupled by the converter into the load train and in that said first gasket and said second gasket as well as the center of the specimen are located at nodes of displacement of said load train where the stress is at a maximum.

4. The apparatus according to claim 1, wherein said first and second feeding means each comprise at least a source of gas having a predetermined composition, a control device to define a predetermined gas pressure, a gas conduit and at least one channel provided in said outer wall of said pressure vessel to be in communication with said first free volume of said first chamber or said second free volume of said second chamber respectively.

5. The apparatus according to claim 4, wherein the first feeding means comprise a first source of gas having a predetermined composition, a control device to define a predetermined gas pressure for the gas taken from the first source of gas, a first gas conduit connected to said first source of gas and to an inlet channel outputting into said first free volume of said first chamber, and an outlet channel in communication with said first free volume of said first chamber and outputting into a second gas conduit connected to said first source of gas, said control device further defining a predetermined gas flow through the first free volume that is larger than a residual leakage flow between the first and second free volumes of the first and second chambers.

6. The apparatus according to claim 1, wherein said longitudinal axis is substantially vertical, the first horn defining an upper horn and the second horn defining a lower horn.

7. The apparatus according to claim 1, wherein the gas to be fed in the first chamber or the second chamber is a pure gas.

8. The apparatus according to claim 1, wherein the gas to be fed in the first chamber or the second chamber is a mixture of different gases components.

9. The apparatus according to claim 1, wherein the gas to be fed in the first chamber or the second chamber comprises at least hydrogen.

10. The apparatus according to claim 1, wherein the first and second horns are designed as members having a generally tapering shape from their base part to their tip which is connected to the specimen.

11. The apparatus according to claim 1, wherein the pressures in the first and second free volumes of said first and second chambers are lower than 1000 bar.

12. The apparatus according to claim 1, wherein the pressures in the first and second free volumes of said first and second chambers are comprised between 200 bar and 500 bar.

13. A method for carrying out, in a controlled atmosphere, material fatigue tests of a specimen in a high cycle regime with a controlled strain ratio with an apparatus according to claim 1, comprising:
  locating a specimen within the first chamber of the apparatus by fixing the one end of the specimen to the tip of the first horn and fixing the opposite end of the specimen to the tip of the second horn,
  feeding gas in the first and second chambers of the pressure vessel such that due to a pressure difference in both first and second chambers a desired static stress is applied to the specimen,
  controlling the converter such that a dynamic stress is applied to the specimen by exciting ultrasonic waves coupled from the converter into the load train, and
  maintaining a nearly constant preset pressure difference between the first and second chambers by controlling the gas flow to the first and second chambers via said first and second feeding means.

14. The method of claim 13, wherein a pure gas is used to feed the first and second free volumes of the first and second chambers and the step of maintaining a nearly constant preset pressure difference between the first and second chambers comprises:
  controlling an exhaust from the one of the first and second chambers having the lower pressure and increasing a gas flow into the other of the first and second chambers having a higher pressure such that a leakage flow between said first and second chambers is compensated.

15. The method of claim 13, wherein a gas mixture is used to feed the first and second free volumes of the first and second chambers and the step of maintaining a nearly constant preset pressure difference between the first and second chambers comprises:
  maintaining a predetermined gas flow through the one of the first and second chambers having the higher pressure, said predetermined gas flow being larger than a leakage flow between the first and the second chambers in order to control a gas composition in said one of the first and second chambers having the higher pressure.

* * * * *